(12) United States Patent
Castillo et al.

(10) Patent No.: US 11,311,207 B2
(45) Date of Patent: Apr. 26, 2022

(54) SYSTEMS AND METHODS FOR PULMONARY VENTILATION FROM IMAGE PROCESSING

(71) Applicant: William Beaumont Hospital, Royal Oak, MI (US)

(72) Inventors: Edward Castillo, Houston, TX (US); Thomas Guerrero, Rochester Hills, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 82 days.

(21) Appl. No.: 16/705,844

(22) Filed: Dec. 6, 2019

(65) Prior Publication Data

US 2020/0178845 A1    Jun. 11, 2020

Related U.S. Application Data

(60) Provisional application No. 62/782,756, filed on Dec. 20, 2018, provisional application No. 62/776,197, filed on Dec. 6, 2018.

(51) Int. Cl.

| | |
|---|---|
| *G06K 9/00* | (2022.01) |
| *A61B 5/091* | (2006.01) |
| *A61B 6/00* | (2006.01) |
| *A61B 5/055* | (2006.01) |
| *A61B 6/03* | (2006.01) |

(Continued)

(52) U.S. Cl.
CPC .............. *A61B 5/091* (2013.01); *A61B 5/055* (2013.01); *A61B 5/743* (2013.01); *A61B 6/032* (2013.01); *A61B 6/463* (2013.01); *G06T 7/0016* (2013.01); *G06T 7/62* (2017.01);
(Continued)

(58) Field of Classification Search
CPC ...................................................... A61B 5/091
See application file for complete search history.

(56) References Cited

U.S. PATENT DOCUMENTS

| | | | |
|---|---|---|---|
| 9,076,201 B1* | 7/2015 | Negahdar | ................. G06T 7/30 |
| 2014/0079304 A1* | 3/2014 | Foo | ........................... G06T 7/11 |
| | | | 382/131 |

(Continued)

OTHER PUBLICATIONS

Albert, MS, et al. Biological magnetic resonance imaging using laser-polarized 129Xe. Nature. 1994;370:199. PubMed PMID: 8028666.

(Continued)

*Primary Examiner* — Oneal R Mistry
(74) *Attorney, Agent, or Firm* — Honigman LLP; Thomas J. Appledorn; Douglas H. Siegel

(57) ABSTRACT

A method for processing images of lungs, the method comprising defining an inhale region of interest of the lungs at an inhale position and an exhale region of interest of the lungs at an exhale position, determining a spatial transformation of each voxel within the lungs between the lungs at the inhale position and the lungs at the exhale position to provide displacement vector estimates for each voxel within the lungs, and performing volume change inference operations to determine a volume change between the lungs at the inhale position and the lungs at the exhale position based on the inhale region of interest, the exhale region of interest, and the displacement vector estimates for each voxel within the lungs.

20 Claims, 11 Drawing Sheets

(51) Int. Cl.
  *G06T 7/00* (2017.01)
  *G06T 7/62* (2017.01)
  *A61B 5/00* (2006.01)
(52) U.S. Cl.
  CPC ............... *G06T 2207/10076* (2013.01); *G06T 2207/10088* (2013.01); *G06T 2207/30061* (2013.01)

(56) References Cited

U.S. PATENT DOCUMENTS

| | | | | |
|---|---|---|---|---|
| 2016/0206848 | A1* | 7/2016 | Glenn | A61B 5/055 |
| 2016/0292864 | A1* | 10/2016 | Dabbah | A61B 6/486 |
| 2018/0070905 | A1* | 3/2018 | El-Baz | A61B 6/486 |
| 2019/0307458 | A1* | 10/2019 | Mathis | A61B 1/00085 |

OTHER PUBLICATIONS

Altes, TA, et al. Hyperpolarized helium-3 magnetic resonance lung imaging of non-sedated infants and young children: a proof-of-concept study. Clin Imaging. 2017;45:105-10.

Bauman, G, et al. Non-contrast-enhanced perfusion and ventilation assessment of the human lung by means of fourier decomposition in proton MRI. Magn Reson Med. 2009;62(3):656-64.

Capaldi, DPI, et al. Free-breathing Pulmonary MR Imaging to Quantify Regional Ventilation. Radiology. 2018;287(2):693-704.

Capaldi, DPI, et al. Free-breathing Functional Pulmonary MRI: Response to Bronchodilator and Bronchoprovocation in Severe Asthma. Acad Radiol. 2017;24(10):1268-76. PubMed PMID: 28551402.

Castillo, R, et al. Ventilation from four-dimensional computed tomography: density versus Jacobian methods. Phys Med Biol. 2010;55(16):4661. PubMed PMID: 20671351.

Guerrero, T, et al. Dynamic ventilation imaging from four-dimensional computed tomography. Phys Med Biol. 2006;51(4):777. PubMed PMID: 16467578.

Guerrero, TM, et al. Quantification of regional ventilation from treatment planning CT. Int J Radiat Oncol Biol Phys. 2005;62(3):630-4. PubMed PMID: 15936537.

Higano, NS, et al. Hyperpolarized 3He Gas MRI in Infant Lungs: Investigating Airspace Size. A98 Seeing is believing: Using novel imaging techniques to understand the lung in health and disease: American Thoracic Society; 2017. p. A2663.

Hoffman, EA, et al. Pulmonary CT and MRI phenotypes that help explain chronic pulmonary obstruction disease pathophysiology and outcomes. J Magn Reson Imaging. 2015;43(3):544-57.

Kern, AL, et al. Hyperpolarized gas MRI in pulmonology. Br J Radiol. 2018;91(1084):20170647.

Middleton, H, et al. MR Imaging with Hyperpolarized 3He Gas. Magn Reson Med. 1995;33(2):271-5. PubMed PMID: 7707920.

Mugler JP, et al. Hyperpolarized 129Xe MRI of the human lung. J Magn Reson Imaging. 2013;37(2):313-31.

Pennati, F, et al. Assessment of Regional Lung Function with Multivolume 1H MR Imaging in Health and Obstructive Lung Disease: Comparison with 3He MR Imaging. Radiology. 2014;273(2):580-90.

Simon, BA. Non-invasive imaging of regional lung function using x-ray computed tomography. J Clin Monit Comput. 2000;16(5-6):433-42. PubMed PMID: 12580227.

Vinogradskiy, Y, et al. Regional Lung Function Profiles of Stage I and III Lung Cancer Patients: An Evaluation for Functional Avoidance Radiation Therapy. Int J Radiat Oncol Biol Phys. 2016;95(4):1273-80.

Wild, JM, et al. Hyperpolarised Helium-3 (3He) MRI: Physical Methods for Imaging Human Lung Function. In: Kauczor H-U, Wielpütz MO, editors. MRI of the Lung. Cham: Springer International Publishing; 2018. p. 69-97. DOI: 10.1007/174_2017_45.

Yamamoto, T, et al. The first patient treatment of computed tomography ventilation functional image-guided radiotherapy for lung cancer. Radiother Oncol. 2016;118(2):227-31. PubMed PMID: 26687903.

Yaremko, BP, et al. Reduction of Normal Lung Irradiation in Locally Advanced Non-Small-Cell Lung Cancer Patients, Using Ventilation Images for Functional Avoidance. Int J Radiat Oncol Biol Phys. 2007;68(2):562-71.

Zha, W, et al. Regional Heterogeneity of Lobar Ventilation in Asthma Using Hyperpolarized Helium-3 MRI. Acad Radiol. 2018;25(2):169-78.

* cited by examiner

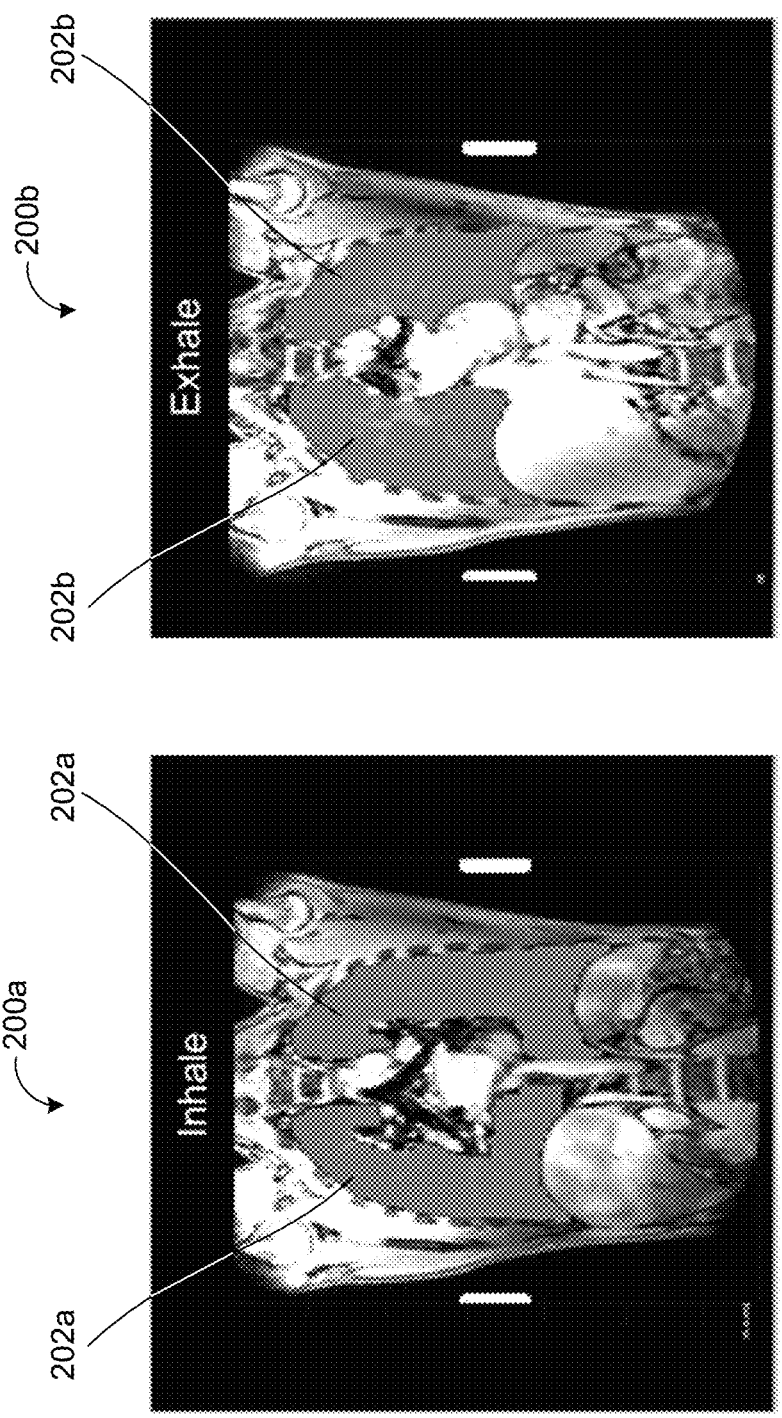

SYSTEMS AND METHODS FOR PULMONARY VENTILATION FROM IMAGE PROCESSING

CROSS REFERENCE TO RELATED APPLICATIONS

This U.S. patent application claims priority under 35 U.S.C. § 119(e) to U.S. Provisional Application 62/776,197, filed on Dec. 6, 2018 and to U.S. Provisional Application 62/782,756, filed on Dec. 20, 2018. The disclosures of these prior applications are considered part of the disclosure of this application and are hereby incorporated by reference in their entireties.

TECHNICAL FIELD

This disclosure relates to systems and methods for pulmonary ventilation from image processing.

BACKGROUND

Magnetic Resonance Imaging (MRI) is a non-invasive imaging technology that is predicated on the alignment of the magnetic poles found in the hydrogen nuclei ($^1$H) from water in a strong magnetic field and their interaction with applied radio waves. The $^1$H's local environment influences their behavior resulting in measurable differences in the signal from various tissues (e.g., muscle, bone, etc.). Tissue types can be differentiated according to how they react to radio pulse sequences, thereby providing a high-resolution, high-contrast volumetric representation of a patient's soft-tissue anatomy. Other nuclei also possess magnetic poles and their alignment can be enhanced. For example, hyperpolarized noble gases, such as $^3$He or $^{129}$Xe, can serve as contrast agents providing a much greater signal than the indigenous $^1$H nuclei, and hyperpolarized noble gases may provide a functional image based on the behavior of inhaled gas. MRI combined with hyperpolarized gases ("Hyp-MRI") functional imaging has been demonstrated to successfully visualize and quantify regions of ventilation and has further demonstrated potential as a metric for quantifying both disease severity and disease progression.

MRI-based ventilation imaging may have some advantages over competing modalities. For instance, nuclear medicine planar V/Q imaging requires radiation exposure and produces only a two-dimensional projection of ventilation. Single Photon Emission Computed Tomography (SPECT) $^{99m}$Tc-DTPA (diethylenetriamine pentaacetate) ventilation also requires radiation exposure, but generates a low-resolution three-dimensional image. However, the $^{99m}$Tc-DTPA aerosol is water soluble, which results in significant deposition artifacts. Despite its advantages, Hyp-MRI has not been adopted into the clinical standard of care. In fact, only a handful of institutions around the world are capable of acquiring Hyp-MRI due to the required specialized MRI expertise needed to perform the scans and the limited availability of hyperpolarized noble gases.

Computed Tomography (CT)-derived ventilation imaging is an image processing based modality, where image segmentation and deformable image registration (DIR) methods are applied to the temporally-resolved phases of a four-dimensional (4D) CT image set or breath-hold CT pair in order to infer the lung voxel volume changes induced by respiratory motion. Since its inception, CT-ventilation has been the subject of numerous validation studies, which primarily focused on comparison with established modalities such as $^{99m}$Tc-DTPA (diethylenetriamine pentaacetate) SPECT-ventilation, $^{99m}$Tc-MAA SPECT-perfusion, $^{68}$Ga-MAA PET perfusion, $^{68}$Ga-nanoparticles PET ventilation, and $^3$He hyperpolarized MRI. The relative success of these studies has led to the development of applications, mainly in radiation oncology, such as functional avoidance radiotherapy planning and treatment response modeling.

There are at least two approaches for computing CT-ventilation: intensity-based and transformation-based. Intensity based methods estimate volume changes directly from the Hounsfield units of spatially corresponding inhale and exhale voxels. Whereas, with transformation-based methods, estimates are derived from the Jacobian factor of the DIR recovered spatial transformation. Variations and combinations of the two approaches have also been proposed.

Regardless of approach, CT-ventilation is computed with image processing methods. As such, its physiological accuracy and clinical utility highly depend on the performance of the employed numerical algorithms. CT-ventilation methods therefore face the same challenges arising in the field of scientific computing, where the goal is to develop numerical methods based on mathematical models of a physical phenomenon. Software implementations require both verification and validation of the numerical method and mathematical models before being confidently deployed in practice. Despite the large number of validation studies, surprisingly little research has focused on the verification of CT-ventilation, which in this case, refers to the characterization of the numerical approximation errors associated with the computation.

Recent work has shown that current methods for transformation-based ventilation, which depend on finite difference approximations applied to the DIR recovered displacement field, are inherently non-stable numerically, meaning that small perturbations to the DIR solution can cause large relative changes in the resulting ventilation image. This property partly explains the reported sensitivity of CT-ventilation with respect to DIR method and 4DCT acquisition artifacts; in addition to its overall poor reproducibility.

The Integrated Jacobian Formulation (IJF) method may be implemented for computing DIR measured volume changes. The IJF method is based on robust estimates of regional volume change, which are computed by applying a sampling method to numerically integrate the regional Jacobian formulation. The resulting volume change estimates 1) respect the restrictions posed by the resolution of the digital grid and 2) have a quantifiable and controllable level of uncertainty. A Jacobian image, which depicts the volume change for each voxel within the reference image, is computed from the regional estimates by solving a constrained linear least squares problem. Two sets of experiments may be used to assess the performance of the IJF method with respect to 1) variable DIR solutions and 2) the correlation between ventilation images generated from 4DCT and 4D cone beam CT acquisitions.

SUMMARY

One aspect of the disclosure provides a method for processing images of lungs. The method includes defining an inhale region of interest of the lungs at an inhale position and an exhale region of interest of the lungs at an exhale position, determining a spatial transformation of each voxel within the lungs between the lungs at the inhale position and the lungs at the exhale position to provide displacement vector estimates for each voxel within the lungs, and performing volume change inference operations to determine a volume change between the lungs at the inhale position and the lungs at the exhale position based on the inhale region of interest, the exhale region of interest, and the displacement vector estimates for each voxel within the lungs.

Implementations of the disclosure may include one or more of the following optional features. In some implementations, the method includes generating and displaying the processed images of the lungs including a color-gradient scale illustrating volumetric ventilation within the defined inhale region of interest of the lungs.

The method may include obtaining the images of the lungs by magnetic resonance imaging (MRI) or by Computed Tomography (CT). The MRI images may be obtained without the use of contrast agents. The images of the lungs may be obtained from breathhold inhale and exhale MRI pairs. The volume change inference operations may include Jacobian operations.

Another aspect of the disclosure provides a system including data processing hardware and memory hardware in communication with the data processing hardware, the memory hardware storing instructions that when executed on the data processing hardware cause the data processing hardware to perform operations comprising defining an inhale region of interest of the lungs at an inhale position and an exhale region of interest of the lungs at an exhale position, determining a spatial transformation of each voxel within the lungs between the lungs at the inhale position and the lungs at the exhale position to provide displacement vector estimates for each voxel within the lungs, and performing volume change inference operations to determine a volume change between the lungs at the inhale position and the lungs at the exhale position based on the inhale region of interest, the exhale region of interest, and the displacement vector estimates for each voxel within the lungs.

Implementations of the disclosure may include one or more of the following optional features. In some implementations, the operations include generating and displaying the processed images of the lungs including a color-gradient scale illustrating volumetric ventilation within the defined inhale region of interest of the lungs.

The operations may include obtaining the images of the lungs by magnetic resonance imaging (MRI) or by Computed Tomography (CT). The MRI images may be obtained without the use of contrast agents. The images of the lungs may be obtained from breathhold inhale and exhale MRI pairs. The volume change inference operations may include Jacobian operations.

Another aspect of the disclosure provides a computer program product encoded on a non-transitory computer readable storage medium comprising instructions that when executed by a data processing apparatus cause the data processing apparatus to perform operations comprising defining an inhale region of interest of the lungs at an inhale position and an exhale region of interest of the lungs at an exhale position, determining a spatial transformation of each voxel within the lungs between the lungs at the inhale position and the lungs at the exhale position to provide displacement vector estimates for each voxel within the lungs, and performing volume change inference operations to determine a volume change between the lungs at the inhale position and the lungs at the exhale position based on the inhale region of interest, the exhale region of interest, and the displacement vector estimates for each voxel within the lungs.

Implementations of the disclosure may include one or more of the following optional features. In some implementations, the operations include generating and displaying the processed images of the lungs including a color-gradient scale illustrating volumetric ventilation within the defined inhale region of interest of the lungs.

The operations may include obtaining the images of the lungs by magnetic resonance imaging (MRI) or by Computed Tomography (CT). The MRI images may be obtained without the use of contrast agents. The images of the lungs may be obtained from temporally resolved 4-dimensional (4D) magnetic resonance imaging (MRI) sequences. The volume change inference operations may include Jacobian operations.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2A is the MRI image of lungs in the inhale position of FIG. 1A with an image segmentation mask superimposed on the image;

FIG. 2B is the MRI image of lungs in the exhale position of FIG. 1B with the image segmentation mask superimposed on the image;

FIG. 5 is an exemplary graphical representation of a voxel transformation map for;

Like reference symbols in the various drawings indicate like elements.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Referring to FIGS. 1-10, systems and methods for processing images of lungs are generally shown. The systems and methods may include certain elements associated with magnetic resonance imaging (MRI) or Computed Tomography (CT)-derived ventilation imaging and image processing methods to produce non-contrast based MRI-ventilation (MR-vent) images and CT ventilation (CT-vent) images, respectively. In some implementations, the systems and methods may produce the images from lungs in a breathhold inhale position 100a and an exhale position 100b. In other implementations, the systems and methods may produce the images from temporally resolved four-dimensional (4D) MRI sequences or 4DCT sequences, e.g., three-dimensional (3D) images across a fourth dimension: time. The systems and methods described herein may provide safer and more efficient means for producing ventilation images.

Figure 1A:
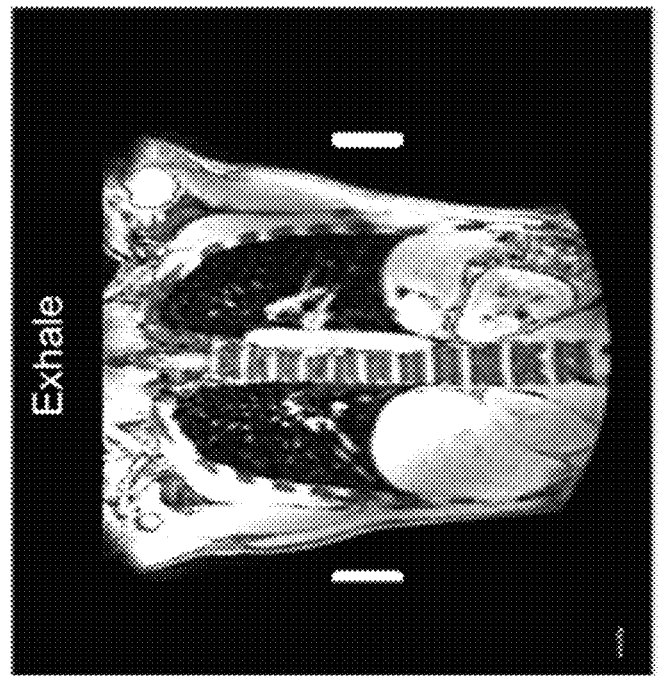
FIG. 1A is an MRI image of lungs in an inhale position.
Figure 1B:
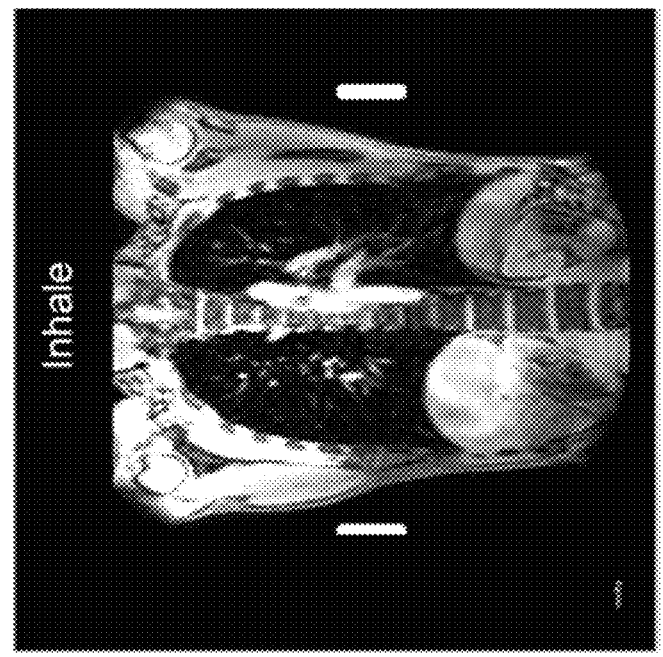
FIG. 1B is an MRI image of lungs in an exhale position.

An image of the lungs in the inhale position 100a is generally shown at FIG. 1A, and an image of the lungs in the exhale position 100b is generally shown at FIG. 1B. The images of the lungs may be obtained by any suitable process, such as, MRI, CT, etc. In some implementations, the images are obtained without the use of contrast agents. The images of the lungs may be obtained in any suitable manner, such as captured by a healthcare provider including a physician, a nurse, etc., or obtained from any suitable third-party individual or entity.

Referring to FIGS. 2A and 2B, images of the lungs in the inhale position 200a and the exhale position 200b, respectively, are generally shown and may illustrate graphical representations of the process of image segmentation. For example, the lungs in the inhale position 200a may include a defined inhale region of interest 202a, and the lungs in the exhale position 200b may include a defined exhale region of interest 202b. The regions of interest 202a, 202b may be defined by locating objects and boundaries and, in some implementations, analyzing each pixel and/or voxel in the images 200a, 200b. The image segmentation may be performed manually or by any suitable analysis, such as machine learning, artificial intelligence, etc.

Figure 3:
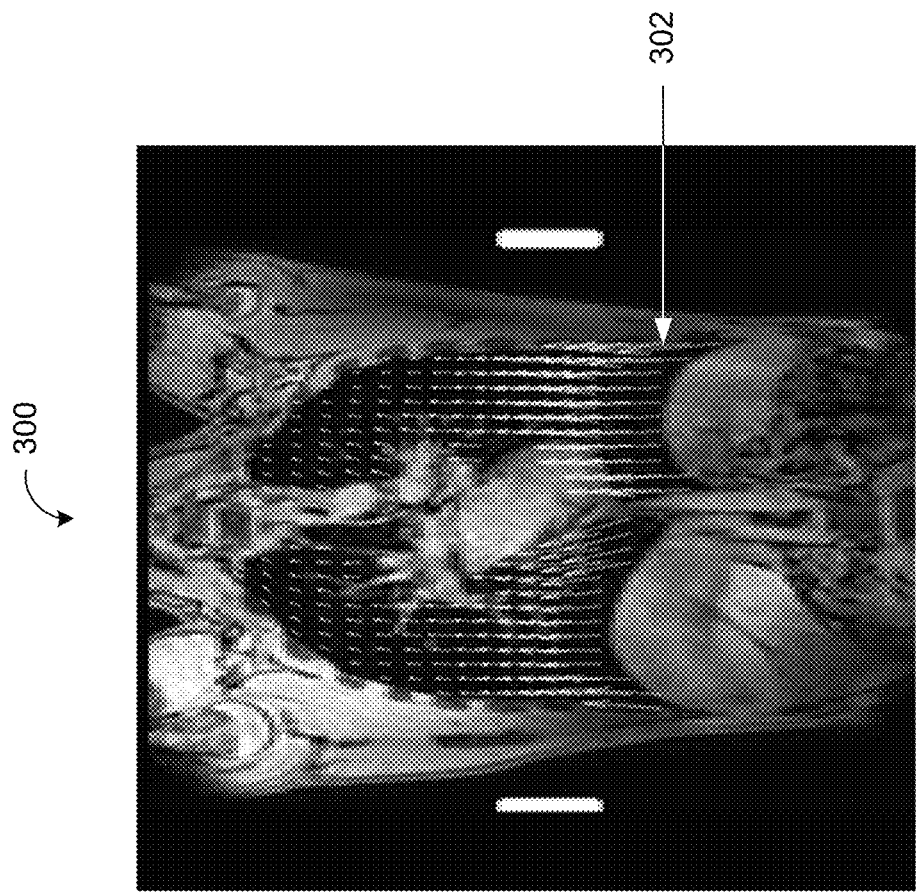
FIG. 3 is the MRI image of lungs in the inhale position of FIG. 1A with a deformable image registration solution superimposed on the image.
Figure 4:
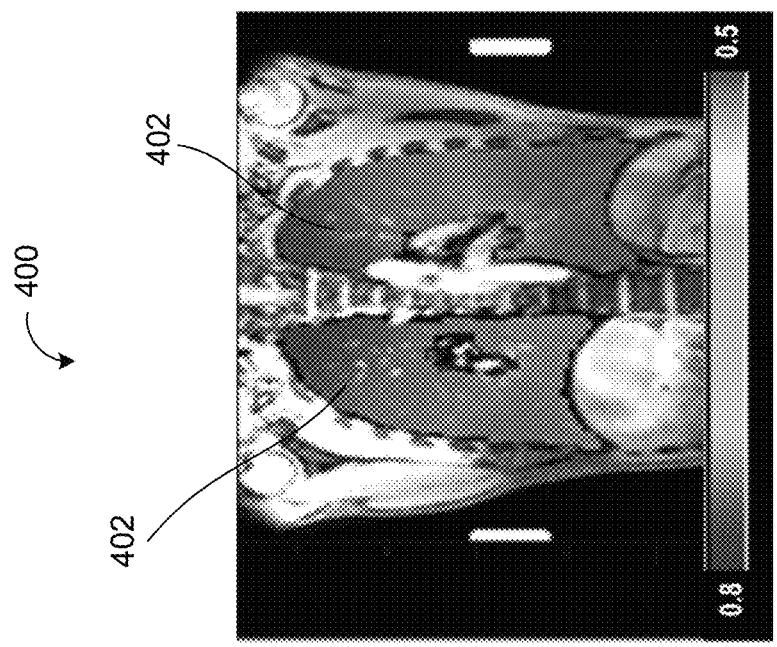
FIG. 4 is the MRI image of the lungs in the inhale position of FIG. 1A with a volumetric ventilation image superimposed on the MRI.

Referring to FIG. 3, an image of the lungs in the inhale position 300 is generally shown and may illustrate a graphical representation of deformable image registration (DIR). For example, DIR may approximate volume changes from a spatial transformation, $\phi$, that describes the apparent lung motion between the inhale position and the exhale position (from breathing) to produce or provide displacement vector estimates 302 for each voxel in the defined regions of interest 202a, 202b of the lungs. The base of each displacement vector 302 represents the location of the voxel at the inhale position and the tip of each displacement vector represents the location of the voxel at the exhale position. As can be seen in FIG. 3, the displacement vectors 302 of each voxel tend to move upward from the inhale position to the exhale position, thus, describing the apparent lung motion between the inhale position and the exhale position. In other implementations, the displacement vectors may be formed from the exhale position to the inhale position. As used herein, when describing "between the inhale position and the exhale position," it should be understood that such language encompasses both from the inhale position to the exhale position and from the exhale position to the inhale position. The spatial transformation may be described in terms of the voxel displacement field:

$$\phi(x)=x+d(x),$$

$$\phi(x):\Omega^{(R)} \to \Omega^{(T)}, \qquad (\text{Eq. 1})$$

where $\Omega^{(R)}$, $\Omega^{(T)} \in \mathbb{R}^3$ represent the regions of interest 202a, 202b within the reference inhale image and the target exhale image respectively. A standard assumption when computing ventilation images is the ability to generate both inhale and exhale lung masks (segmentations), which implies that $\Omega^{(R)}$, $\Omega^{(T)}$ are both known and contain the same lung tissue. The true spatial transformation may not be known, therefore, it may be approximated numerically with a DIR algorithm. The resulting DIR solution may provide the displacement vector estimates 302 for the voxels in $\Omega^{(R)}$, as shown in FIG. 3 and/or the masks as shown in the series of images 700 in FIG. 7. The DIR may be performed manually or by any suitable analysis, such as DIR algorithm employment, machine learning, artificial intelligence, etc.

Referring to FIGS. 4 and 7-9, processed images 400, 700, 800, 900 of the lungs may include a color gradient scale 402 illustrating volumetric ventilation within the defined inhale region of interest 202a of the lungs.

Figure 7:
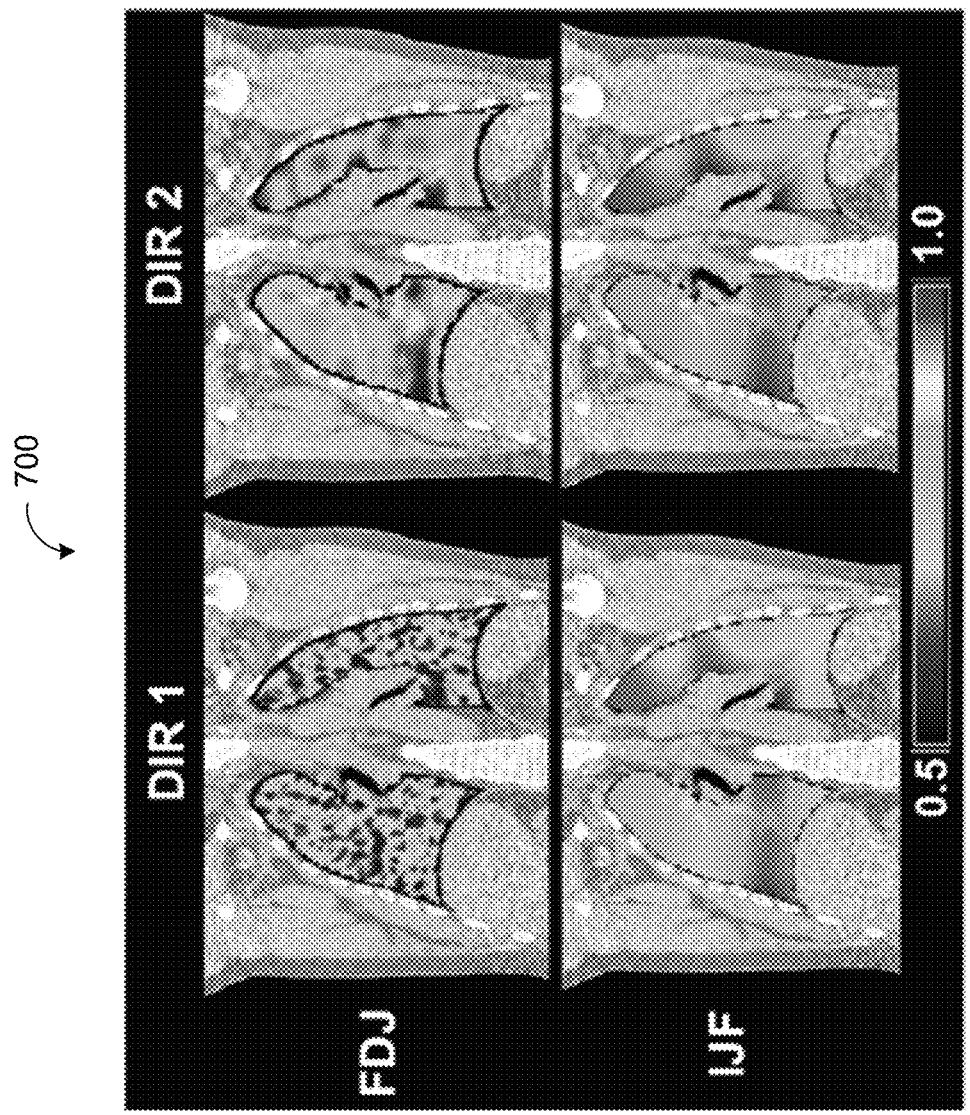
FIG. 7 is a series of CT images of lungs with a first and a second deformable image registration solution superimposed on the images using FDJ and IJF.

Referring to FIG. 7, the finite difference Jacobian (FDJ) images (top) and the Integrated Jacobian Formulation (IJF) images (bottom) may be computed for the same case with two DIR solutions. While there may be a substantial visual difference between the two FDJ images, the IFJ images are nearly identical. The color gradient scale reflects the fact that inhale to exhale motion is primarily a contraction, e.g., voxel volumes may shrink.

Figure 8:
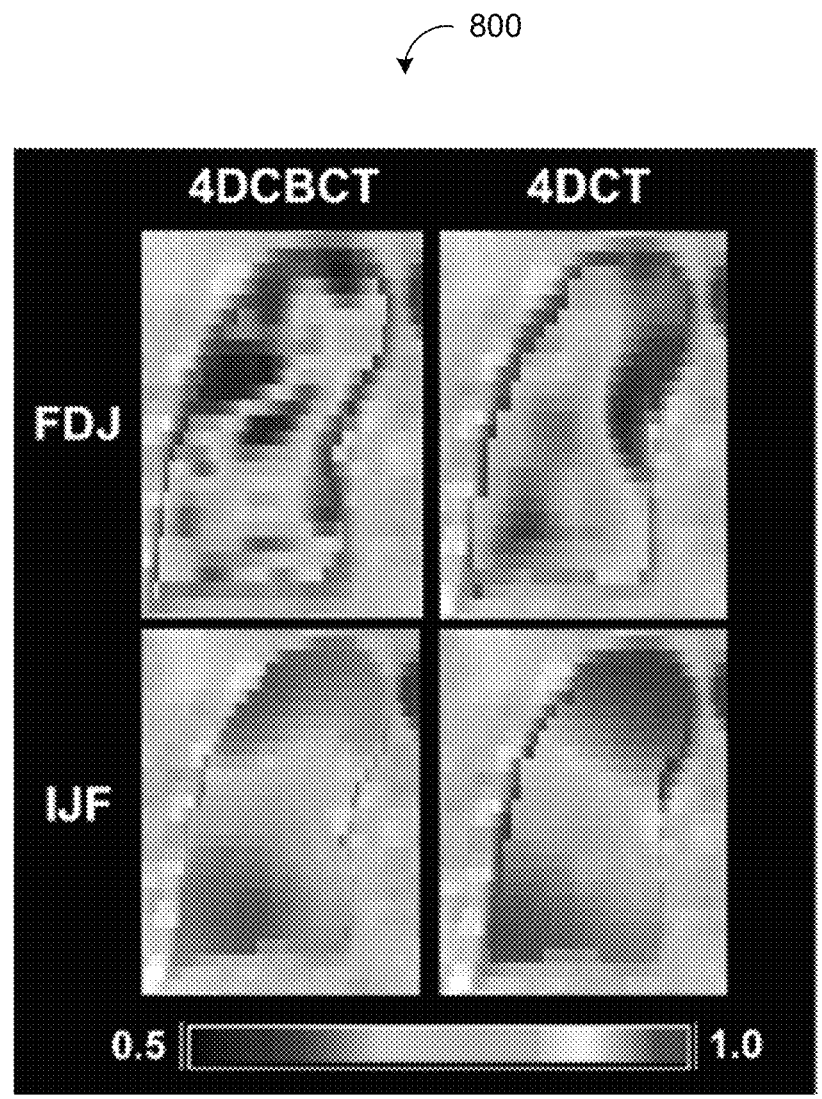
FIG. 8 is a series of images of lungs created from 4DCBCT and 4DCT using FDJ and IJF.

Referring to FIG. 8, the FDJ images (top) and the IFJ images (bottom) may be computed from four-dimensional cone beam CT (4DCBCT) images and four-dimensional CT (4DCT) images for the same patient, superimposed on the inhale CBCT phase. The 4DCT FDJ and IFJ images may be mapped onto the inhale CBCT phase via affine registration. While there may be a substantial difference between the FDJ images (e.g., Pearson correlation 0.41), the IJF images may be very similar (Pearson correlation 0.95). The color gradient scale reflects the fact that inhale to exhale motion is primarily a contraction, e.g., voxel volumes may shrink.

Figure 9:
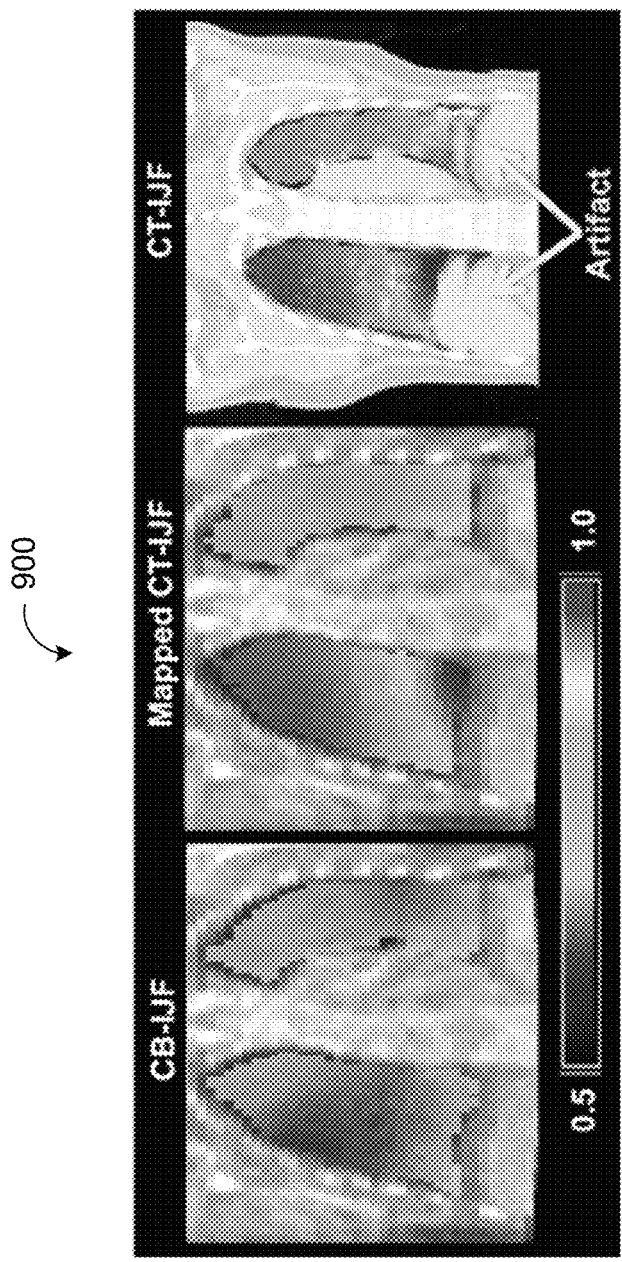
FIG. 9 is a series of images of lungs created from 4DCBCT, CT-IJF mapped onto an inhale CBCT phase, and 4DCT.

Referring to FIG. 9, the CB-IJF image may be created from the 4DCBCT (left) and the CT-IJF image may be created from radiotherapy planning 4DCT (right) for a lung patient. The mapped CF-IJF image (middle) may depict the CT-IJF image mapped onto the inhale CBCT phase. The 4DCT image (right) contains a large phase binning artifact at the diaphragm, resulting in significant variation between the CB-IJF and CT-IJF images. The color gradient scale reflects the fact that inhale to exhale motion is primarily a contraction, e.g., voxel volumes may shrink.

Referring to FIGS. 4 and 7-9, the volumetric ventilation may be calculated by performing volume change inference operations, such as, Jacobian, J(x), operations.

The Jacobian, J(x), is the first full derivative of $\phi$:

$$J(x) = \begin{bmatrix} \frac{\partial \phi_1(x)}{\partial x_1} & \frac{\partial \phi_1(x)}{\partial x_2} & \frac{\partial \phi_1(x)}{\partial x_3} \\ \frac{\partial \phi_2(x)}{\partial x_1} & \frac{\partial \phi_2(x)}{\partial x_2} & \frac{\partial \phi_2(x)}{\partial x_3} \\ \frac{\partial \phi_3(x)}{\partial x_1} & \frac{\partial \phi_3(x)}{\partial x_2} & \frac{\partial \phi_3(x)}{\partial x_3} \end{bmatrix}, \qquad (\text{Eq. 2})$$

and it describes the volume scaling factor under $\phi$:

$$\int_\Omega |\det(J(x)| dx = \text{vol}(\phi(\Omega)), \qquad (\text{Eq. 3})$$

where $\Omega \subseteq \Omega^{(R)}$ and $\phi(\Omega) \subseteq \Omega^{(T)}$ is the image of $\Omega$ under $\phi$. For medical imaging applications, $\phi$ is assumed to be diffeomorphic, which implies:

$$\det(J(x)) > 0, \forall x \in \Omega^{(R)}. \tag{Eq. 4}$$

Computing a MR-ventilation image or a volumetric transformation-based CT ventilation image requires numerically approximating the integral in Eq. 3 for a series of different subvolumes within $\Omega^{(R)}$. Current methods take $\Omega_i$, to be the unit voxel volume centered on $x_i^2$. This allows for a volumetric midpoint rule approximation of the Eq. 3 integral:

$$Vol(\phi(\Omega_i)) = \int_{\Omega_i} \det(J(x_i)) dx \approx \det(J(x_i)) \frac{Vol(\Omega_i)}{1} = \det(J(x_i)). \tag{Eq. 5}$$

Figure 5:
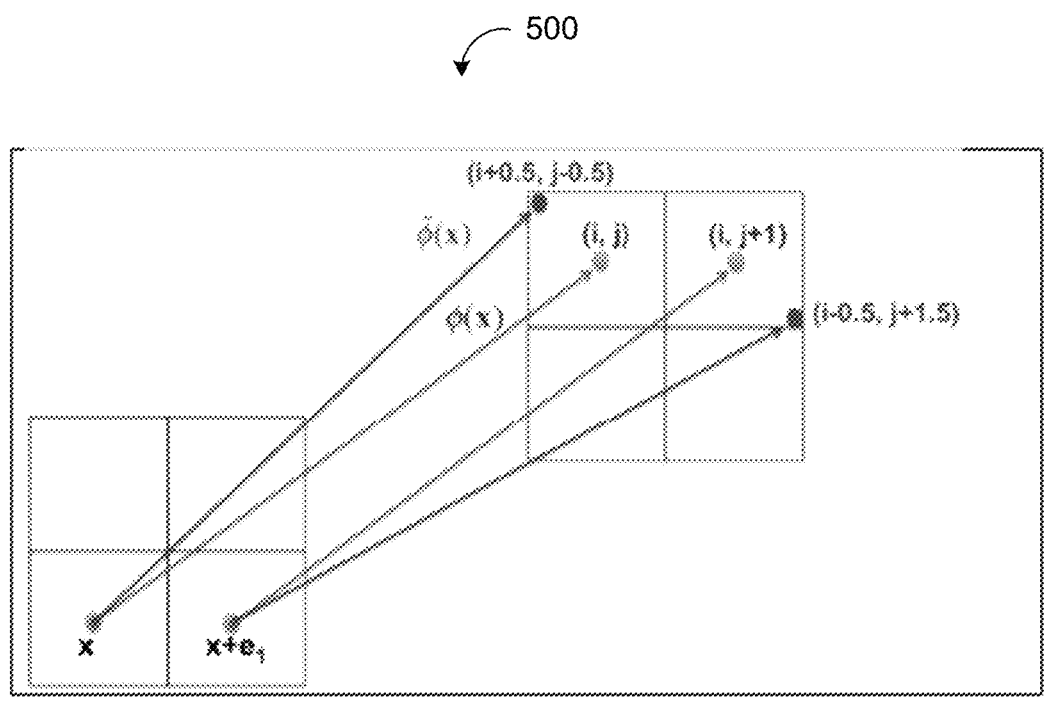

Since voxels are spaced uniformly on the digital grid, the partial derivatives given by Eq. 2 can be approximated with a finite difference scheme, which may be referred to as the finite difference Jacobian (FDJ):

$$Vol(\phi(\Omega_i)) \approx \det(\hat{J}(x_i)), \tag{Eq. 6}$$

Where the entries in $\hat{J}(x_i)$ are obtained with forward difference approximations:

$$\frac{\partial \phi_i(x_k)}{\partial x_j} \approx \phi_i(x_k + e_j) - \phi_i(x_k), \tag{Eq. 7}$$

and $e_j$ is a standard basis vector. Small perturbations to the DIR displacement field may cause large relative changes in the FDJ volume change estimate. The result follows from the fact that the general finite difference approximation error is $O(h)$, where h is equal to the grid spacing. In the case of the digital voxel grid h=1, which implies that the uncertainty in the Eq. 7 finite difference approximation is ±1. Intuitively, this uncertainty stems from the fact that DIR spatial accuracy resolution is limited to the digital grid. In other words, using expert-determined landmarks it is possible to determine if a reference voxel is mapped into the correct target voxel volume, but it is not possible to determine where within the target voxel the correctly mapped point lies. Consequently, finite difference approximations can vary by as much as 1.0 for displacement estimates with the exact same spatial accuracy, as illustrated by FIG. 5. This result is problematic since inhale to exhale lung motion is primarily a contraction, meaning that the relative voxel volume change values are in general less than or equal to 1.0, and therefore, well within the error margin of the FDJ approximation.

For a general subdomain $\Omega \in \Omega^{(R)}$, Eqs. 3-5 imply:

$$vol(\phi(\Omega)) = \int_\Omega \det(J(x)) dx = \Sigma_{x_i \in \Omega} v_i, \tag{Eq. 8}$$

where the discretized variables $$v_i = \det(J(x_i)), v_i > 0, \tag{Eq. 9}$$

reflect that volume change is strictly positive.

FDJ methods directly estimate each $v_i$ with finite differences and $O(1)$ uncertainty. Rather than depending on finite differences to estimate volume changes for individual voxels, robust regional volume change measurements may be implemented by approximating $vol(\phi(\Omega))$ using a "hit-or-miss" algorithm, which is a sampling method that can be viewed theoretically as a simpler variant of the Monte Carlo integration method. Briefly, the method does not require an explicit representation of $\phi(\Omega)$ to estimate $vol(\phi(\Omega))$. Since $\phi$ is assumed to be diffeomorphic, $\phi^{-1}$ exists and can be used to define a voxel membership oracle. In this case, the membership oracle answers the question: "Given an $x \in \Omega^{(T)}$, is $x \in \phi(\Omega)$?" Mathematically, the membership oracle is defined $\forall x \in \Omega^{(T)}$ as:

$$f(x; \Omega, \phi) = \begin{cases} 1, & \text{if } \phi^{-1}(x) \in \Omega, \\ 0, & \text{otherwise.} \end{cases} \tag{Eq. 10}$$

Since $\Omega$ represents a region of voxel volumes within $\Omega^{(R)}$, the oracle essentially operates on the components of $\phi^{-1}$ rounded to the nearest integer values. Or more specifically, $$\phi^{-1}(x) \in \Omega \Leftrightarrow [\phi^{-1}(x)] \in \Omega, \tag{Eq. 11}$$

where $[\phi^{-1}(x)]$ represents the component-wise rounding operation. As such, the oracle evaluations are equivalent for two DIR solutions with the same spatial accuracy.

The hit-or-miss method first computes the sampled average of the oracle function over an enclosing region with known volume. Since $\Omega^{(T)}$ is known and $\phi(\Omega) \subseteq \Omega^{(T)}$, the estimated function average, $\langle f \rangle$, is given as:

$$\langle f \rangle = \frac{H}{N}, H = \sum_{x_i \in \Omega^{(T)}} f(x_i; \phi, \Omega), \tag{Eq. 12}$$

where $N = |\Omega^{(T)}|$ and H is the number of voxels that "hit" $\phi(\Omega)$. The corresponding volume estimation is then computed as the ratio of hits to samples multiplied by the volume of the enclosing region:

$$vol(\phi(\Omega)) \approx \langle f \rangle N = H \tag{Eq. 13}$$

Combining Eqs. 8 and 13 results in a simple linear equation that relates individual voxel volume changes within $\Omega$ to the hit-or-miss volume approximation:

$$\Sigma_{x_i \in \Omega} v_i = H. \tag{Eq. 14}$$

Since N is assumed to be large, similar to Monte Carlo error analysis, adopting Gaussian statistics allows for the uncertainty in the Eq. 12 average function value, and consequently the Eq. 13 volume estimation, to be characterized by the standard error of the mean:

$$s_{\langle f \rangle} = \frac{s}{\sqrt{N}}, \tag{Eq. 15}$$

where s is the sample standard deviation. Applying Eq. 15 to the estimated mean in Eq. 12 yields:

$$s_{\langle f \rangle} = \sqrt{\frac{\langle f^2 \rangle - \langle f \rangle^2}{N-1}} = \sqrt{\frac{H/N - (H/N)^2}{N-1}}. \tag{Eq. 16}$$

Thus, the uncertainty in the Eq. 13 hit-or-miss volume estimate can be expressed as:

$$vol(\phi(\Omega)) \approx E_{x_i \in \Omega^{(T)}} f(x_i; \phi, \Omega) \pm \beta N s_{\langle f \rangle}. \tag{Eq. 17}$$

Eq. 17 provides a probabilistic assessment of the volume approximation in terms of a confidence interval defined by the parameter $\beta$. For instance, setting $\beta = 1.96$ implies that with 95% probability:

$$|vol(\phi(\Omega)) - H| \leq \beta N s_{\langle f \rangle}. \tag{Eq. 18}$$

Figure 6:
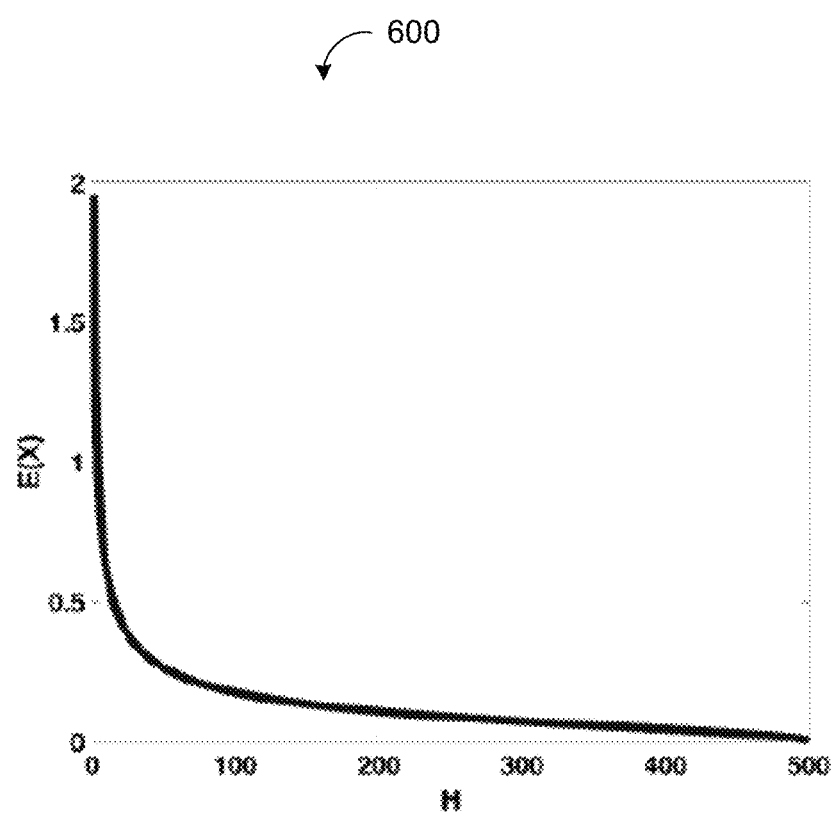
FIG. 6 is an exemplary graphical representation of a relative uncertainty in hit-or-miss volume change estimate.

General Monte Carlo methods reduce the uncertainty by raising the number of point samples, which implies the oracle function is precise for any sampling resolution. In this case, the problem is inherently discretized by the digital grid. Consequently, both DIR spatial accuracy and the Eq. 10 oracle are limited to the grid resolution. Therefore, the number of samples $N=|\Omega^{(T)}|$ is fixed and the Eq. 18 uncertainty is determined solely by the number of hits H. FIG. 6 shows that the relative uncertainty function for fixed N:

$$E(H, \beta) = \frac{\beta N s_{(f)}}{H}. \quad \text{(Eq. 19)}$$

is monotonically decreasing with respect to H. For H=1, the uncertainty is approximately 100%, which mimics the O(1) error of forward finite differences. Conversely, the most trusted volume measurement is that of the complete target segmentation mask: $N=|\Omega^{(T)}|$.

Given a β* corresponding to a specified confidence level and a desired relative error T, there exists a unique H*≤N such that:

$$E(H,\beta^*) \leq \tau, \forall H \geq H^*. \quad \text{(Eq. 20)}$$

This result follows from the fact that E is monotonically decreasing and E(H,β*)=1.

A full MR-ventilation or CT-ventilation image, V(x), may require computing the discretized variables:

$$V(x_i) = v_i = \det(J(x_i)), \forall x_i \in \Omega^{(R)}. \quad \text{(Eq. 21)}$$

This algorithm is built on the idea of computing enough regional estimates to define a full rank, under-determined, or over-determined linear system of equations for the M unknowns. Applying Eq. 14 to a series of subregions $\Omega_k \in \Omega^{(R)}$, k=1, 2, . . . , K results in the following linear system:

$$Cv = b, C \in \mathbb{R}^{K \times M}, b \in \mathbb{R}^{K \times 1}, v \in \mathbb{R}^{M \times 1}, \quad \text{(Eq. 22)}$$

where $$C_{ki} = \begin{cases} 1, & \text{if } x_i \in \Omega_k \\ 0, & \text{otherwise} \end{cases}, \quad \text{(Eq. 23)}$$

and the elements of b are computed according to Eq. 13:

$$b_k = \Sigma_{x_i \in \Omega^{(T)}} f(x_i; \phi, \Omega_k). \quad \text{(Eq. 24)}$$

If the subregions are allowed to overlap, Eq. 22 is similar in structure to a standard image de-blurring problem. Though in this case, the volume change image recovery problem is defined on an irregular domain, i.e., the lung regions of interest 202a, 202b, while de-blurring problems are typically defined on the full image domain.

The Eq. 22 subregions can be constructed to satisfy the uncertainty bound given by Eq. 20, but the resulting $H_k$ data values are still approximations. As such, Eq. 22 should not be treated as a hard constraint. However, global volume change, as measured by the volumes of the inhale/exhale masks, is often used as a validation metric for proposed ventilation methods. Thus, the global mass change:

$$\Sigma_{i=1}^M v_i = |\Omega^{(T)}| = N \quad \text{(Eq. 25)}$$

can be enforced as a hard constraint. Eqs. 22 and 25 may not be guaranteed to provide enough information to uniquely determine v. Therefore, a two-norm penalization on the spatial gradient of V(x) is employed to both induce smoothness in the reconstructed image and guarantee the existence of a unique solution (i.e. regularize the problem). However, any regularization approach, such as total variation or Tikhonov, can be used. Combining these assumptions results in the following constrained linear least squares problem, the solution of which is the recovered volume change image:

$$\min_v \frac{1}{2} \|Cv - b\|^2 + \frac{\alpha}{2} \sum_{i=1}^M \|\nabla V(x_i)\|^2 \quad \text{(Eq. 26)}$$

$$\text{s.t. } \sum_{i=1}^M v_i = N,$$

$$v_i \geq \epsilon, i = 1, 2, \ldots, M.$$

The penalty parameter α dictates the amount of smoothness in the solution v* and the lower bound ∈>0 represents the minimum possible voxel volume. Eq. 26 may be referred to as the Integrated Jacobian (IJ) method for computing DIR induced volume changes and transformation-based ventilation. The regularization strategy used in Eq. 26 may be interchangeable, for example, total variation may be implemented.

It should be understand that the aforementioned equations and operations are exemplary in nature and variations are contemplated. Further, certain operations may be added or omitted, and the operations may be performed in any suitable order.

Figure 10:
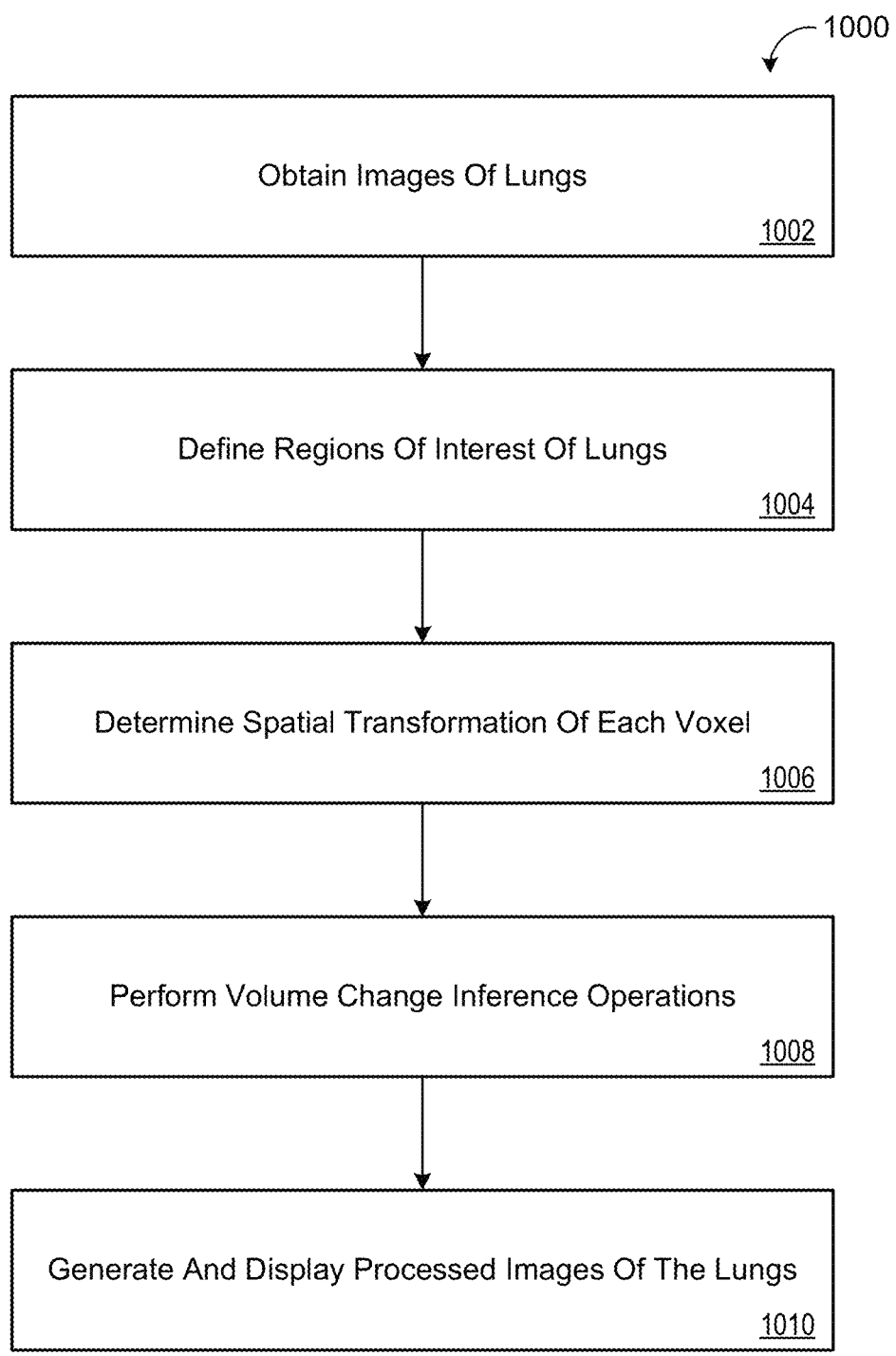
FIG. 10 is flowchart illustrating a method for processing images of lungs.

FIG. 10 refers to an exemplary flowchart for a method 1000 for processing images of lungs. It should be understood that the steps for the method 1000 described herein may be performed in any suitable order, and additional or fewer steps may be implemented. At step 1002, images of the lungs may be obtained by capturing the images via MRI, CT, or any other suitable method, obtaining the images from a third party, or obtaining the images in any other suitable manner. The regions of interest 202a, 202b are defined in step 1004, as shown in FIGS. 2A and 2B. The spatial transformation of each voxel is calculated 1006 and the displacement vectors 302 are provided, as shown in FIG. 3. The volume change inference operations, such as Jacobian operations, are performed at step 1008. The images of the lung ventilation as shown in FIGS. 5A-5C are generated and displayed including a color-gradient scale illustrating ventilation magnitude within the defined inhale region of interest 202a of the lungs.

Figure 11:
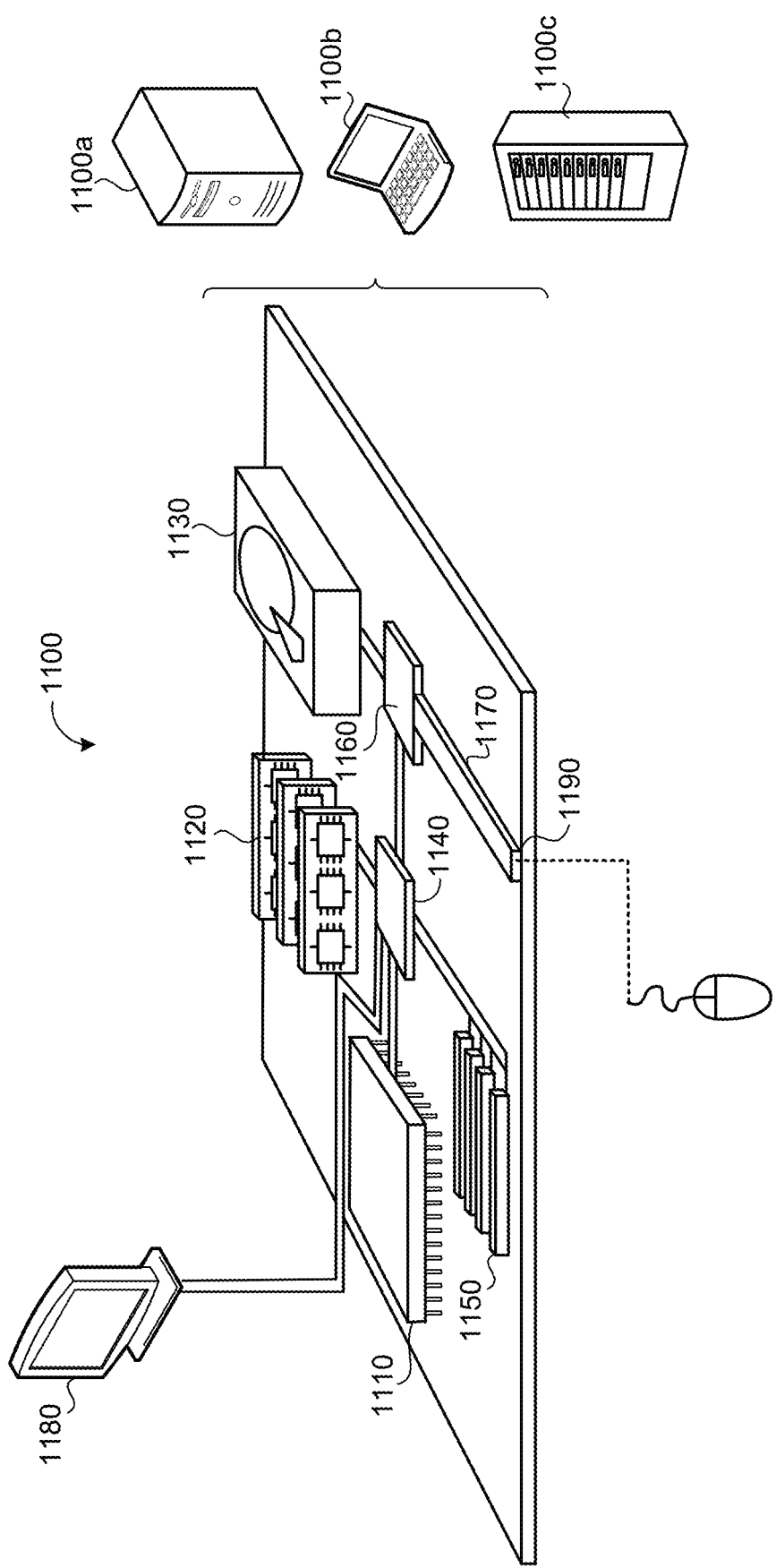
FIG. 11 is a schematic view of an example computing device that may be used to implement the systems and methods described herein.

FIG. 11 is schematic view of an example computing device 1100 that may be used to implement the systems and methods described in this document. The computing device 1100 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 1100 includes a processor 1110, memory 1120, a storage device 1130, a high-speed interface/controller 1140 connecting to the memory 1120 and high-speed expansion ports 1150, and a low speed interface/controller 1160 connecting to a low speed bus 1170 and a storage device 1130. Each of the components 1110, 1120, 1130, 1140, 1150, and 1160, are interconnected using various busses, and may be mounted on a common motherboard or in other manners as appropriate. The processor 1110 can process instructions for execution within the computing device 1100, including instructions stored in the memory 1120 or on the storage device 1130 to display graphical information for a graphical user interface (GUI) on an external input/output device, such as display 1180 coupled to high speed interface 1140. In other implementations, multiple processors and/or multiple buses may be used, as appropriate, along with multiple memories and types of memory. Also, multiple computing devices 1100 may be connected, with each device providing portions of the necessary operations (e.g., as a server bank, a group of blade servers, or a multi-processor system).

The memory 1120 stores information non-transitorily within the computing device 1100. The memory 1120 may be a computer-readable medium, a volatile memory unit(s), or non-volatile memory unit(s). The non-transitory memory 1120 may be physical devices used to store programs (e.g., sequences of instructions) or data (e.g., program state information) on a temporary or permanent basis for use by the computing device 1100. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 1130 is capable of providing mass storage for the computing device 1100. In some implementations, the storage device 1130 is a computer-readable medium. In various different implementations, the storage device 1130 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 1120, the storage device 1130, or memory on processor 1110.

The high speed controller 1140 manages bandwidth-intensive operations for the computing device 1100, while the low speed controller 1160 manages lower bandwidth-intensive operations. Such allocation of duties is exemplary only. In some implementations, the high-speed controller 1140 is coupled to the memory 1120, the display 1180 (e.g., through a graphics processor or accelerator), and to the high-speed expansion ports 1150, which may accept various expansion cards (not shown). In some implementations, the low-speed controller 1160 is coupled to the storage device 1130 and a low-speed expansion port 1190. The low-speed expansion port 1190, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1100a or multiple times in a group of such servers 1100a, as a laptop computer 1100b, or as part of a rack server system 1100c.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method for processing images of lungs, the method comprising:
   defining an inhale region of interest of the lungs at an inhale position and an exhale region of interest of the lungs at an exhale position;
   determining a spatial transformation of each voxel within the lungs between the lungs at the inhale position and the lungs at the exhale position to provide displacement vector estimates for each voxel within the lungs; and
   performing volume change inference operations to determine a volume change between the lungs at the inhale position and the lungs at the exhale position based on the inhale region of interest, the exhale region of interest, and the displacement vector estimates for each voxel within the lungs, the determined volume change having a quantifiable and controllable level of uncertainty.

2. The method of claim 1, further comprising generating and displaying the processed images of the lungs including a color-gradient scale illustrating volumetric ventilation within the defined inhale region of interest of the lungs.

3. The method of claim 1, further comprising obtaining the images of the lungs by magnetic resonance imaging (MRI).

4. The method of claim 1, further comprising obtaining the images of the lungs by Computed Tomography (CT).

5. The method of claim 1, wherein the images of the lungs are obtained by MRI without the use of contrast agents.

6. The method of claim 1, wherein the volume change inference operations include Jacobian operations.

7. The method of claim 1, wherein the images of the lungs are obtained from breathhold inhale and exhale magnetic resonance imaging (MRI) pairs.

8. A system comprising:
   data processing hardware; and
   memory hardware in communication with the data processing hardware, the memory hardware storing instructions that when executed on the data processing hardware cause the data processing hardware to perform operations comprising:
      defining an inhale region of interest of lungs at an inhale position and an exhale region of interest of the lungs at an exhale position;
      determining a spatial transformation of each voxel within the lungs between the lungs at the inhale position and the lungs at the exhale position to provide displacement vector estimates for each voxel within the lungs; and
      performing volume change inference operations to determine a volume change between the lungs at the inhale position and the lungs at the exhale position based on the inhale region of interest, the exhale region of interest, and the displacement vector estimates for each voxel within the lungs, the determined volume change having a quantifiable and controllable level of uncertainty.

9. The system of claim 8, wherein the operations include generating and displaying processed images of the lungs including a color-gradient scale illustrating volumetric ventilation within the defined inhale region of interest of the lungs.

10. The system of claim 8, wherein the operations include obtaining the images of the lungs by magnetic resonance imaging (MRI).

11. The system of claim 8, wherein the operations include obtaining the images of the lungs by Computed Tomography (CT).

12. The system of claim 10, wherein the images of the lungs are obtained by MRI without the use of contrast agents.

13. The system of claim 8, wherein the volume change inference operations include Jacobian operations.

14. The system of claim 8, wherein the images of the lungs are obtained from breathhold inhale and exhale magnetic resonance imaging (MRI) pairs.

15. A computer program product encoded on a non-transitory computer readable storage medium comprising instructions that when executed by a data processing apparatus cause the data processing apparatus to perform operations comprising:
   defining an inhale region of interest of lungs at an inhale position and an exhale region of interest of the lungs at an exhale position;
   determining a spatial transformation of each voxel within the lungs between the lungs at the inhale position and the lungs at the exhale position to provide displacement vector estimates for each voxel within the lungs; and
   performing volume change inference operations to determine a volume change between the lungs at the inhale position and the lungs at the exhale position based on the inhale region of interest, the exhale region of interest, and the displacement vector estimates for each voxel within the lungs, the determined volume change having a quantifiable and controllable level of uncertainty.

16. The computer program product of claim 15, wherein the operations include generating and displaying processed images of the lungs including a color-gradient scale illustrating volumetric ventilation within the defined inhale region of interest of the lungs.

17. The computer program product of claim 15, wherein the operations include obtaining the images of the lungs by magnetic resonance imaging (MRI) without the use of contrast agents.

18. The computer program product of claim 15, wherein the operations include obtaining the images of the lungs by Computed Tomography (CT).

19. The computer program product of claim 15, wherein the volume change inference operations include Jacobian operations.

20. The computer program product of claim 15, wherein the images of the lungs are obtained from temporally resolved 4-dimensional (4D) magnetic resonance imaging (MRI) sequences.

\* \* \* \* \*